(12) United States Patent
Luukanen et al.

(10) Patent No.: US 10,495,585 B2
(45) Date of Patent: Dec. 3, 2019

(54) IMAGING APPARATUS FOR MONITORING OBJECTS (71) Applicant: Asqella Oy, Helsinki (FI)

(72) Inventors: Arttu Luukanen, Helsinki (FI); Mikko Leivo, Helsinki (FI); Anssi Rautiainen, Espoo (FI); Aleksi Tamminen, Helsinki (FI)

(73) Assignee: ASQELLA OY, Helsinki (FI)

( * ) Notice: Subject to any disclaimer, the term of this patent is extended or adjusted under 35 U.S.C. 154(b) by 0 days.

(21) Appl. No.: 15/363,092

(22) Filed: Nov. 29, 2016

(65) Prior Publication Data

US 2017/0160210 A1   Jun. 8, 2017

(30) Foreign Application Priority Data

Dec. 4, 2015   (EP) .................................... 15197914

(51) Int. Cl.
*G01N 22/00* (2006.01)
*G01V 8/00* (2006.01)

(52) U.S. Cl.
CPC ............. *G01N 22/00* (2013.01); *G01V 8/005* (2013.01); *G01N 2223/101* (2013.01); *G01N 2223/3302* (2013.01); *G01N 2223/413* (2013.01); *G01N 2223/501* (2013.01)

(58) Field of Classification Search
CPC .......................... G01N 21/3581; G01N 22/00
See application file for complete search history.

(56) References Cited

U.S. PATENT DOCUMENTS

| | | | | |
|---|---|---|---|---|
| 6,652,452 B1 * | 11/2003 | Seifert | ............... | A61B 1/00096 600/140 |
| 9,528,881 B1 * | 12/2016 | Dawson | .................... | G01J 5/20 |
| 2002/0148982 A1 | 10/2002 | Tatum et al. | | |
| 2008/0078935 A1 | 4/2008 | Bijwaard | | |
| 2011/0221599 A1 | 9/2011 | Hogasten | | |

FOREIGN PATENT DOCUMENTS

CN   104898171 A   9/2015

OTHER PUBLICATIONS

Grossman et al. "Active Millimeter-wave Imaging for Concealed Weapons Detection", Electromagnetic Technology Division, National Institute of Standards and Technology, Boulder, CO, Passive Millimeter-Wave Imaging Technology VI and Radar Sensor Technology VII, Roger Appleby, David A. Wikner, Robert Trebits, James L. Kurtz, Editors, Proceedings of SPIE vol. 5077, Aug. 25, 2003, 10 pages.

(Continued)

*Primary Examiner* — Michael C Bryant
(74) *Attorney, Agent, or Firm* — Ziegler IP Law Group, LLC (57) ABSTRACT An imaging apparatus that includes a scanning mirror arrangement, optics, and a detector arrangement comprising a plurality of detectors. The plurality of detectors are capable for detecting submillimeter-/millimeter-range electromagnetic radiation and arranged within a region defined by an outer periphery and an inner periphery of the detector arrangement. The outer and inner peripheries are substantially circular in shape.

19 Claims, 5 Drawing Sheets

(56) References Cited

OTHER PUBLICATIONS

Grossman et al. "Concealed Weapons Detection using an Uncooled Millimeter-wave Microbolometer System", Electromagnetic Technology Division, National Institute of Standards and Technology, Boulder, CO, Infrared and Passive Millimeter-wave Imaging Systems: Design, Analysis, Modeling, and Testing, Roger Appleby, Gerald C. Holst David A. Wikner, Editors, Proceedings of SPIE vol. 4719, Apr. 1, 2002, 6 pages.
International Search Report and Written Opinion of the International Searching Authority, Application No. PCT/EP2016/078557, dated Feb. 7, 2017, 14 pages.
Glenn et al. "Bolocam: A millimeter-wave bolometic camera" Optical Sensing II, vol. 3357, Jul. 31, 1998, ISSN: 0277-786X, DOI: 10.117/12.317418, ISBN: 978-1-62841-971-9 9 pages.
Heinz et al. "Development of passive submillimeter-wave video imaging systems for security applications", Optical Sensing II, vol. 8544, Oct. 26, 2012, ISSN: 0277-786X, DOI: 10.1117/12.976849, ISBN: 978-1-62841-971-9, 8 pages.
Extended European Search Report, Application No. 15197914.3-1559, dated Jun. 15, 2016, 10 pages.
The State Intellectual Property Office of China, First Office Action, Application No. 201680003128.0, dated Jun. 5, 2018, 10 pages.

\* cited by examiner

IMAGING APPARATUS FOR MONITORING OBJECTS

TECHNICAL FIELD

The present disclosure relates generally to security devices; and more specifically, to an imaging apparatus for monitoring or scanning concealed objects.

BACKGROUND

Millimeter-wave cameras (also known as Terahertz cameras) are well known in the art. Typically, the millimeter wave cameras are used for full body scanning of people for security purposes and/or to prevent commercial losses, smuggling and the like. Such millimeter wave cameras may be deployed, for example, at airports, government buildings or commercial buildings. Specifically, such millimetre-wave cameras may be used for detecting objects concealed underneath a person's clothing by detecting electromagnetic radiation emitted from the objects.

Figure 1A:
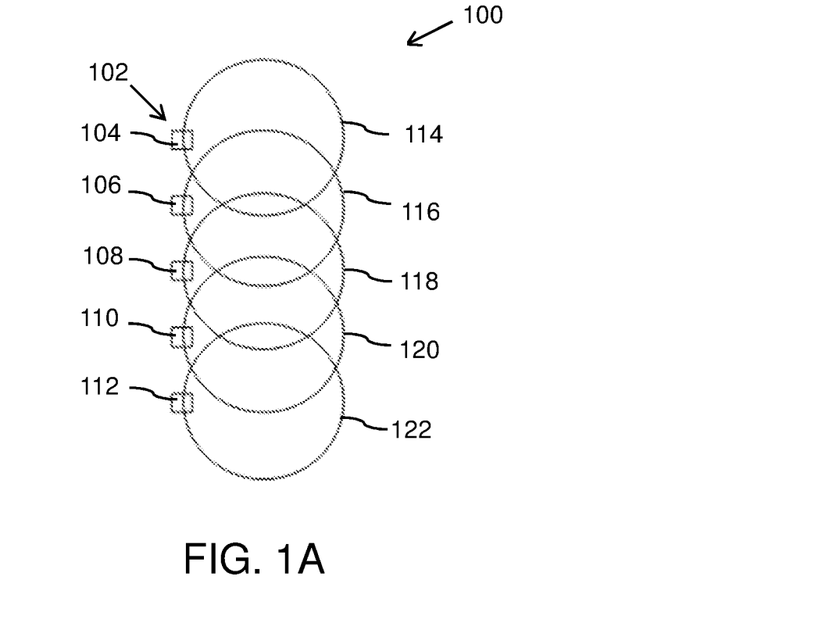
FIG. 1A is an example illustration of a scan pattern obtained from a linear detector arrangement for image formation, in accordance with an embodiment of the present disclosure.
Figure 1B:
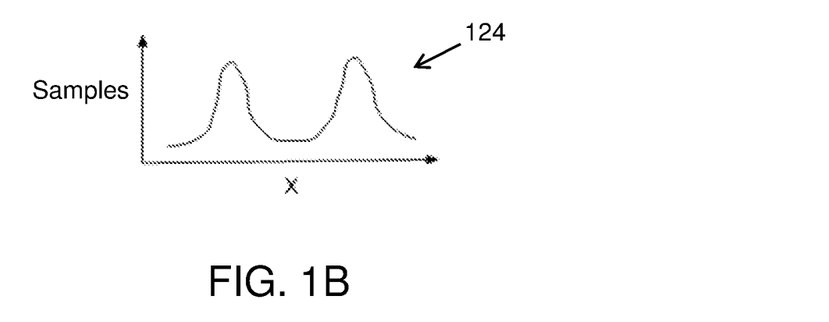
FIG. 1B is a graphical representation of the scan pattern sampling density based on detection by the detector arrangement of FIG. 1A, in accordance with an embodiment of the present disclosure.

Typically, such millimetre-wave cameras use complex technology and require special arrangements, such as cooling close to 4 Kelvin temperature. Further, a detector arrangement of such cameras is expensive to manufacture and require relatively large amount of space. In an example, for emitted electromagnetic waves of say wavelength $\lambda=1$ mm, dimensions of a detector has to be in a range of greater than or equal to 0.5 mm. Therefore, creating an image with decent resolution, such as a resolution of 640×480, would require an area of at least 320 mm×240 mm for the detector arrangement. One way to overcome such issues is to arrange the detectors linearly. However, the linear arrangement of the detectors results in an image having an sub-optimal sampling density in the middle portion of the field of view. Further, a scan pattern for image formation using the linear arrangement of the detectors is illustrated in FIGS. 1A-1B. Moreover, for such arrangement, rotation of an image (without rotating the entire camera) may result in loss of some potential information.

Therefore, in light of the foregoing discussion, there exists a need to overcome the aforementioned drawbacks of conventional millimeter wave cameras.

SUMMARY

The present disclosure seeks to provide an imaging apparatus.

The present disclosure further seeks to provide a method for monitoring objects using an imaging apparatus.

In one aspect, an embodiment of the present disclosure provides an imaging apparatus for scanning an object, comprising:
  a scanning mirror arrangement;
  optics; and
  a detector arrangement comprising a plurality of detectors, wherein
    the plurality of detectors are capable for detecting submillimeter-/millimeter-range electromagnetic radiation and;
    the plurality of detectors are arranged within a region defined by an outer periphery and an inner periphery, the outer and inner peripheries being approximately circular in shape.

In another aspect, an embodiment of the present disclosure provides a method for monitoring objects, via an imaging apparatus comprising a detector arrangement having a plurality of detectors, the method comprising:
  directing electromagnetic radiations emitting from the object to be monitored using a scanning mirror arrangement;
  detecting the electromagnetic radiation using the plurality of detectors arranged within a region defined by an outer periphery and an inner periphery of the detector arrangement, the outer and inner peripheries being approximately circular in shape; and
  processing signals received from the plurality of detectors to generate an image of at least one object being monitored by the imaging apparatus.

Embodiments of the present disclosure substantially eliminate or at least partially address the aforementioned problems in the prior art, and provides scanned image of uniform quality.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The terms "connected" or "coupled" and related terms are used in an operational sense and are not necessarily limited to a direct connection or coupling. Thus, for example, two devices may be coupled directly, or via one or more intermediary media or devices. As another example, devices may be coupled in such a way that information can be passed there between, while not sharing any physical connection with one another. Based on the present disclosure provided herein, one of ordinary skill in the art will appreciate a variety of ways in which connection or coupling exists in accordance with the aforementioned definition.

The phrases "in an embodiment", "in accordance with an embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment.

If the specification states a component or feature "may", "can", "could", or "might" be included or have a characteristic, that particular component or feature is not required to be included or have the characteristic.

In one aspect, an embodiment of the present disclosure provides an imaging apparatus for scanning an object, comprising:
  a scanning mirror arrangement;
  optics; and
  a detector arrangement comprising a plurality of detectors, wherein
    the plurality of detectors are capable for detecting submillimeter-/millimeter-range electromagnetic radiation; and
    the plurality of detectors are arranged within a region defined by an outer periphery and an inner periphery, the outer and inner peripheries being circular in shape.

In another aspect, an embodiment of the present disclosure provides a method for monitoring objects, via an imaging apparatus comprising a detector arrangement having a plurality of detectors, the method comprising:
  directing electromagnetic radiations emitting from the object to be monitored using a scanning mirror arrangement;
  detecting electromagnetic radiation using the plurality of detectors arranged within a region defined by an outer periphery and an inner periphery of the detector arrangement, the outer and inner peripheries being approximately circular in shape; and
  processing signals received from the plurality of detectors to generate an image of at least one object being monitored by the imaging apparatus.

In an embodiment, the imaging apparatus is a scanning device, for scanning human body, to find any concealed object carried by them. In an example, the imaging apparatus may be a passive camera configured to receive emitted electromagnetic radiation of the person and any object (which may be carried by the person) with help of electromagnetic radiation detectors. Specifically, the electromagnetic radiation from the person and the object are collected to construct an image of the person and the object. In the present disclosure, the term "object" used herein may be used to either collectively refer to the person and object; or to the object only. Further, the detectors of the imaging apparatus may operate on a temperature sensing principle, and as radiometric temperatures of objects depend on metallic or dielectric properties, the imaging apparatus may easily detect concealed objects, which may include weapons or explosive materials. The imaging apparatus may be deployed, for example, at airports, government buildings or commercial buildings for security purposes and/or to prevent commercial losses, smuggling and the like.

In the present description, by the term "circular" are meant both exactly circular elements to which the term refers but also elements that are approximately or substantially circular.

According to an embodiment, the imaging apparatus may include support arrangement for supporting and receiving the scanning mirror arrangement, the optics and the detector arrangement therein. Further, such imaging apparatus may allow people to pass through while scanning. Alternatively, the imaging apparatus may include a housing for receiving the scanning mirror arrangement, the optics and the detector arrangement therein. Moreover, such imaging apparatus may allow people to move from front thereof while scanning. Also, the imaging apparatus of the present disclosure is operable to scan an object (for example, a concealed object carried by a person) by collecting and analyzing millimeter/submillimeter-range electromagnetic radiation emitting from the object. For example, the millimeter/submillimeter-range electromagnetic radiation may include wavelength in a range of ten to one millimeter as well as sub millimeter.

As mentioned above, the imaging apparatus comprises the scanning mirror arrangement. In an embodiment, the scanning mirror arrangement includes a scanning mirror and an actuator for moving the scanning mirror to direct electromagnetic radiation emitted from the object towards the optics and the plurality of detectors. For example, the scanning mirror may be a flat mirror or a spherical mirror, wherein a spherical mirror is a concave or convex shaped mirror having a circular form. According to a preferred embodiment, the scanning mirror is a flat mirror. The scanning mirror is configured to scan an object based on a movement provided by the actuator to the scanning mirror. The scanning mirror can also use more than one actuator, such as two, three, four, five or six actuators. It is to be understood that in the present description, by the term "actuator", both singular and plural are meant.

In an embodiment, the actuator may be arranged at a back side of the scanning mirror. For example, the actuator may be an arrangement of electronic and mechanical components configured to move the scanning mirror. In one embodiment, the actuator may be operated by a control unit communicably coupled thereto. The control unit may be also communicably coupled to a processing unit (described later). The actuator is configured to rotate the scanning mirror, based on instruction received from the control unit. For example, the actuator may be operated using some software-program (executable on the control unit) for controlling the movement of the scanning mirror. Therefore, the actuator may be responsible for moving the scanning mirror for scanning the object present in an instantaneous field of view.

In one embodiment, the term "field of view" used herein generally refers to a volume in space for which the imaging apparatus is sensitive to electromagnetic radiation. Further, the term "instantaneous field of view" used herein may refer to a volume in space for which an imaging apparatus is sensitive to electromagnetic radiation at any given instant, for example, when people passing through any security check. Therefore, the scanning mirror of the scanning mirror arrangement may be responsible for directing (or reflecting) the electromagnetic radiation emitting from a person or object (which may include, for example, people passing through any security check) or anything such as object which is the volume in space in front of the field of view of the imaging apparatus) towards the focusing optics and detectors of the imaging apparatus.

In an embodiment, the scanning mirror arrangement is arranged to move in a manner such that the detector arrangement (described later) does not move when the scanning mirror arrangement moves. The movement may be rotation or lateral movement. Specifically, another actuator, namely a scanning mirror arrangement actuator (or several mirror arrangement actuators) is configured to move (or rotate) the entire scanning mirror arrangement (the scanning mirror actuator comprising the actuator and the mirror) for directing the electromagnetic radiations emitting from the object to be scanned, while the detector arrangement remains in a fixed position. In other words, the scanning mirror may be further moved for altering the instantaneous field of view in order to cover a required scanning area for which the imaging apparatus is responsible. Specifically, the alteration of the instantaneous field of view is performed using another actuator responsible for moving (or rotating) the entire scanning mirror arrangement. Therefore, the scanning mirror arrangement actuator, responsible for moving the entire scanning mirror arrangement, enables in covering (or scanning) the required scanning area without moving the entire imaging apparatus.

According to an embodiment, the optics may include at least one movable mirror. For example, the optics may be an arrangement of optical component (such as mirrors) and electromechanical component (such as electrical motors) capable of moving the optical component. Further, the optics, particularly, the electromechanical component thereof, may be operated using some software-program for controlling a movement of the optical component. The optics is operable to adjust focus of the electromagnetic radiation coming (or reflected) from the scanning mirror towards the detector arrangement. For example, the optics may be movably adjusted to attain a position that allows required focus for the electromagnetic radiation on the detector arrangement. Specifically, the movable adjustment of the optics, alters focal length thereof, for suitably focusing the electromagnetic radiation on the detector arrangement.

According to an embodiment, the detector arrangement is enclosed in a detector chamber of the imaging apparatus. The plurality of detectors is arranged within a region defined by an outer periphery and an inner periphery of the detector arrangement. In one embodiment, the outer and inner peripheries are approximately circular in shape. For example, the outer and inner peripheries of the detector arrangement may be configured to have elliptical shape, oval shape and the like.

In one embodiment, a ratio of a radius of the outer periphery to a radius of the inner periphery lies in a range between 1.5 and 2. Alternatively, the range for ratio of the radius of the outer periphery to the radius of the inner periphery may be different, from the range of 1.5 and 2, for example 1.25 to 2.5.

According to an embodiment, the plurality of detectors is arranged substantially symmetrically about an optical axis of the optics. In other words, the detector arrangement is spaced apart from the optics, and the optical axis of the optics passes through a center of the detector arrangement.

In one embodiment, the detector arrangement may be a continuous circular loop having the outer periphery and the inner periphery and accommodating the detectors between the outer and inner peripheries. Alternatively, the detector arrangement may include a plurality of detector sets (or elements), each having a plurality of detectors, arranged substantially close to each other for forming the circular loop. According to an embodiment, the imaging apparatus further comprises a processing unit coupled to the detector arrangement. According to yet another embodiment, the plurality of detectors are forming a circular loop, i.e. they are arranged in a form of a circular loop.

According to an embodiment, the plurality of detectors may comprise at least a first type of detectors and a second type of detectors. Alternatively, the plurality of detectors may comprise multiple types, such as first, second, third and fourth type of detectors.

In one embodiment, the type of detectors may be associated with different sizes. For example, the first type of detectors is larger in size than the second type of detectors. Further, the size of a given detector corresponds to a wavelength of electromagnetic radiation detected by the given detector. For example, the detector having larger size may be configured to detect wavelength of electromagnetic radiation having longer wavelength, and the detector having smaller size may be configured to detect wavelength of electromagnetic radiation having smaller wavelength.

In an embodiment, the first type of detectors (larger in size) may be arranged towards the inner periphery of the region, and the second type of detectors (smaller in size) may be arranged towards the outer periphery of the region. In other words, the second type of detectors is arranged away from a center of the detector arrangement as compared to the first type of detectors. In an embodiment, each of the first type of detectors and the second type of detectors might not be at a uniform linear distance from the center. As mentioned above, the outer and inner peripheries are substantially circular in shape, therefore, the first type of detectors and the second type of detectors are arranged in a circular manner.

In another embodiment, the first type of detectors may be arranged towards the outer periphery of the region, and the second type of detectors may be arranged towards the inner periphery of the region. In other words, the first type of detectors is arranged away from the center of the detector arrangement as compared to the second type of detectors. In one embodiment, the third and fourth type of detectors may be arranged within the first and second type of detectors. The detector arrangement of the present disclosure (having different sizes or types, and numbers of detectors) enables in tuning the detector arrangement to be sensitive to various wavelengths of electromagnetic radiation (that may be emitted by objects) for providing images of the objects with greater information content.

In an embodiment, the detectors (i.e. the first, the second, the third and the fourth type) are, for example, transition edge bolometers made from a superconducting material comprising metals, ceramics, organic materials, heavily doped semiconductors that conduct electricity without resistance and the like. Further, operation temperature of such detectors can be very low such as 4 Kelvins. In practice, the detector arrangement (i.e. the detector chamber) is cooled down with Helium and vacuumed with pressures in range of $10^{-6}$ bar or lower.

In one embodiment, the plurality of detectors is configured to detect the millimeter/submillimeter-range electromagnetic radiation. Specifically, the millimeter/submillimeter-range electromagnetic radiation emitting (for example, from the object) gets reflected by the scanning mirror for being forwarded to the optics. Thereafter, the optics focuses the received electromagnetic radiation to the plurality of detectors arranged in the detector arrangement.

In an embodiment, the imaging apparatus further comprises a processing unit coupled to the plurality of detectors (i.e. the detector arrangement). Specifically, each of the sets of detectors (or plurality of detector elements) includes a connector for electrically coupling detectors thereof to the processing unit. For example, the connector may be an electrical cable.

According to an embodiment, the processing unit is configured to process signals received from the detector arrangement to generate an image of at least one object, which is monitored (or scanned) by the imaging apparatus. For example, the processing unit is configured to amplify the signals received from the detector arrangement and further perform calculations to generate the image of the object. In an embodiment, the calculations may be performed using various kinds of image processing algorithms, which may be executed by the processing unit.

In another embodiment, the processing unit is configured to send raw data or pre-processed data (of the detector arrangement), to a server for further processing, via a communication network. For example, the server is configured to perform processing of the pre-processed data received from the processing unit to generate the image of the object. By a server in this description are meant computers, servers, field programmable gate arrays (FPGAs) and graphics processing units (GPUs), as well as other suitable systems and devices. The server may be integrated to the apparatus or it may be a separate apparatus.

In an embodiment, the imaging apparatus further comprises a remote terminal configured to view the generated image of the object. The remote terminal may be communicably coupled to either the processing unit or the server via the communication network for viewing the generated image of the object. In an example, the communication network may be a collection of individual networks, interconnected with each other and functioning as a single large network. Such individual networks may be wired, wireless, or a combination thereof. Examples of such individual networks include, but are not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, Worldwide Interoperability for Microwave Access (WiMAX) networks, and short-range wireless communications network, such as a "Bluetooth" network ("Bluetooth" is a registered trademark).

In one embodiment, a user interface of the remote terminal may be used for viewing the generated image of the object. For example, the remote terminal may include, but are not limited to, smart telephones, Mobile Internet Devices (MIDs), tablet computers, Ultra-Mobile Personal Computers (UMPCs), phablet computers, Personal Digital Assistants (PDAs), web pads, Personal Computers (PCs), handheld PCs, laptop computers, desktop computers, large-sized touch screens with embedded PCs, and other interactive devices, such as Television (TV) sets. In an example, the remote terminal may be associated with security personnel looking for concealed objects for security purposes.

For illustration purposes only, there will now be considered an example of how the at least one object is monitored for screening and security purposes pursuant to embodiments of the present disclosure.

In a first example, when a person is at an entrance of a security screening zone, where the imaging apparatus is employed, the instantaneous field of view of a scanning mirror is steered towards the entrance with the help of an actuator, responsible for moving the scanning mirror arrangement. Further, another actuator is responsible for moving the scanning mirror of the scanning mirror arrangement for scanning objects present in the instantaneous field of view. Further, the millimeter/submillimeter-range electromagnetic radiation emitted from a person (object present in the instantaneous field of view) fall on the scanning mirror, which then moves to a detector arrangement (having a plurality of detectors) via the optics. The plurality of detectors detects the incoming millimeter/submillimeter-range electromagnetic radiations, and forwards the millimeter/submillimeter-range electromagnetic radiations to a processing unit, which processes these radiations and generates an image of the person. In the process, if the person is carrying some concealed object underneath his/her clothing, then it may be viewed by security personnel responsible for viewing the images of the person on a user interface of a remote terminal.

The present disclosure provides an imaging apparatus for monitoring (or scanning) concealed objects. Specifically, the imaging apparatus is capable of scanning human body to detect and in some cases, also to identify any concealed object carried by them. The imaging apparatus includes a detector arrangement having substantially circular shape, which enables in providing uniform scanned images for the objects. Further, the detector arrangement includes various type (or sizes) of detectors capable of detecting a range of wavelengths of electromagnetic radiation. This enables in tuning the detector arrangement to be sensitive to various wavelengths of electromagnetic radiation (generally emitted by objects) for providing images of the objects with greater information content. Moreover, a scanning mirror arrangement of the imaging apparatus is configured to rotate alone (instead of rotation of the entire imaging apparatus). This enables in eliminating image quality issues, which may be caused by vibrations, due to the rotation of the entire imaging apparatus. A further advantage is that as smaller amounts of material is required to be moved, the apparatus can function faster than the known apparatuses.

DETAILED DESCRIPTION OF THE DRAWINGS

Referring to FIG. 1A, illustrated is an example illustration of a scan pattern 100 obtained from a linear detector arrangement 102 for image formation, in accordance with an embodiment of the present disclosure. As shown, the detector arrangement 102 comprises a plurality of detectors, such as detectors 104, 106, 108, 110 and 112 arranged linearly. The detectors 104-112 are configured to receive electromagnetic radiation transmitted from an object (not shown) for the image formation thereof. For example, the transmitted electromagnetic radiation from the object may be focused on the detectors 104-112 via optics (which in turn receives reflected electromagnetic radiation from at least one mirror, not shown). The scan pattern 100 comprises circular scans 114-122 corresponding to the detectors 104-112 respectively.

Referring now to FIG. 1B, illustrated is a graphical representation 124 of the scan pattern 100 based on the detector arrangement 102, in accordance with an embodiment of the present disclosure. The detection from the linear detector arrangement 102 results in an uneven accuracy for a generated image. As shown, in the graph 124, number of samples is higher for edges of the image compared to a middle portion of the image. Further, the rotation (or change) of a point of view with the optics, may cause rotation of the image losing potential information associated with the image.

Figure 2:
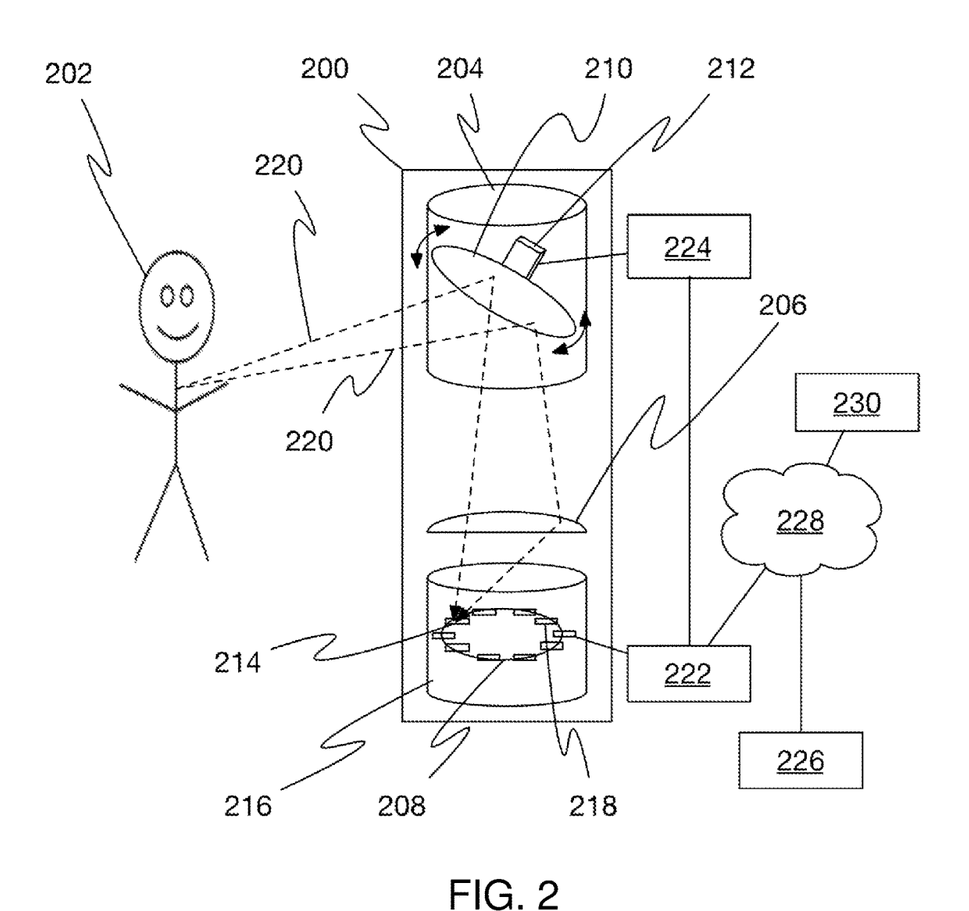
FIG. 2 is a schematic illustration of an environment for incorporating various embodiments of the present disclosure.

Referring to FIG. 2, illustrated is a schematic illustration of an environment for incorporating various embodiments of the present disclosure. The environment comprises an imaging apparatus 200 configured to monitor a person 202. The imaging apparatus 200 comprises a scanning mirror arrangement 204, optics 206 and a detector arrangement 208. The scanning mirror arrangement 204 comprises a scanning mirror 210 and an actuator 212 responsible for moving the scanning mirror 210. The imaging apparatus 200 may also include another actuator (not shown) responsible for moving the entire scanning mirror arrangement 204. The detector arrangement 208 comprises a plurality of detectors 214. Specifically, the detector arrangement 208 is enclosed in a detector chamber 216 configured to house the plurality of detectors 214 therein.

As shown (with a dotted line), electromagnetic radiation 220 emitting from the person 202 falls on the scanning mirror 210, which directs the electromagnetic radiation 220 towards the plurality of detectors 214 via the optics 206. The plurality of detectors 214 is configured to detect the electromagnetic radiation 220 and send data (associated with the electromagnetic radiation 220) to a processing unit 222 communicably coupled to the plurality of detectors 214. The processing unit 222 is configured to process the data (associated with the electromagnetic radiation 220) to generate an image of the person 202.

The processing unit 222 is further communicably coupled to a control unit 224 which is configured to control the actuator 212. The actuator 212 is configured to rotate the scanning mirror 210, based on instruction received from the control unit 224. Further, another actuator (not shown) is configured to rotate the entire scanning mirror arrangement 204 without rotating the entire imaging apparatus 200 while monitoring (or scanning) the person 202. The processing unit 222 is further configured to send raw data or pre-processed data to a server 226, for further processing, via a communication network 228. The generated image can be viewed on a user interface of a remote terminal 230 over the communication network 228.

Figure 3A:
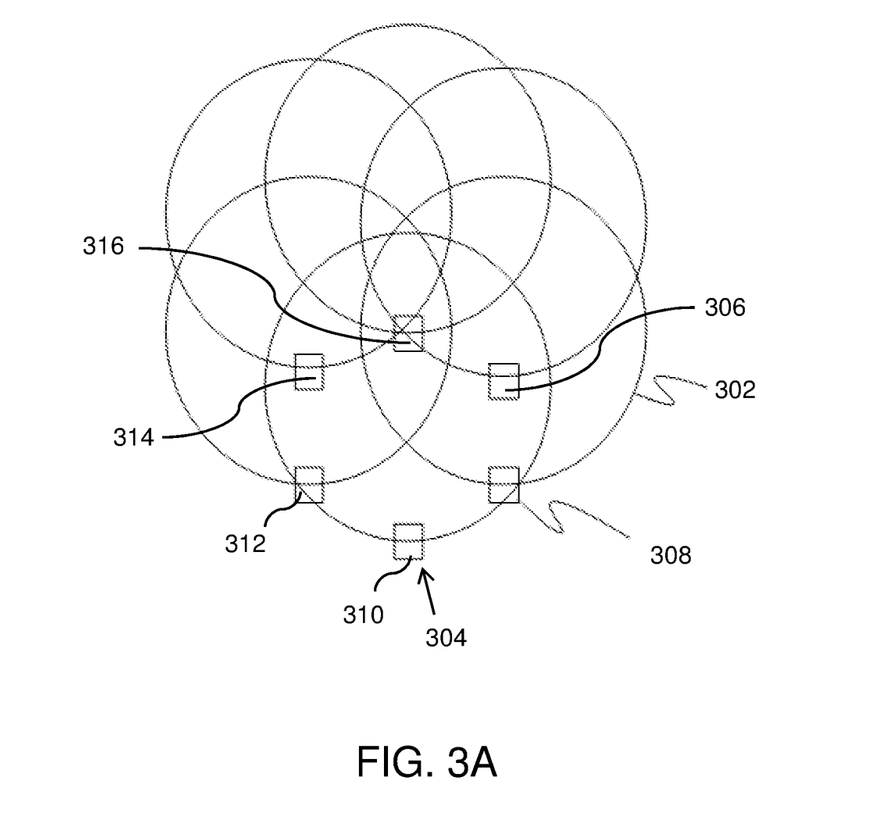
FIG. 3A is a schematic illustration of a scan pattern obtained from a circular detector arrangement, in accordance with an embodiment of the present disclosure.

Referring now to FIG. 3A, illustrated is a schematic illustration of a scan pattern 302 obtained from a circular detector arrangement 304, in accordance with an embodiment of the present disclosure. As shown, the detector arrangement 304 comprises a plurality of detectors, such as detectors 306-316 arranged in a circular manner. Each of the detectors 306-316 scans and detects the electromagnetic radiation (such as the electromagnetic radiation 220 emitting from the person 202, shown in FIG. 2) for forming the scan pattern 302. Based on the detection of the detectors 306-316, an image is generated thereafter.

Figure 3B:
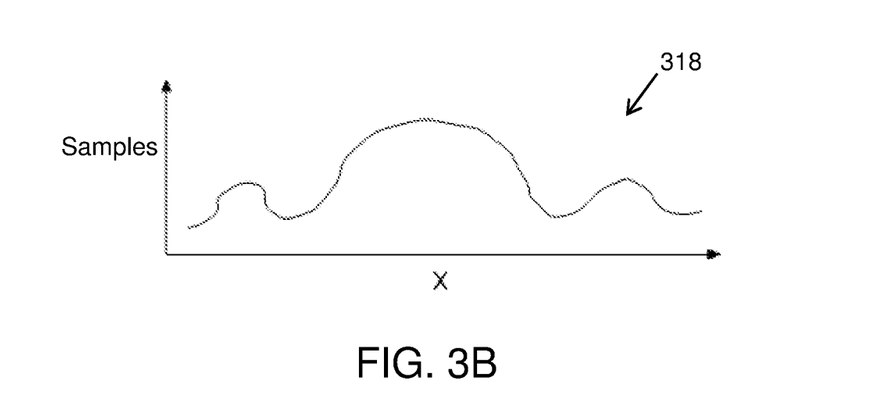
FIG. 3B is a graphical representation of the scan pattern sampling density based on detection by the detector arrangement of FIG. 3A, in accordance with an embodiment of the present disclosure.

Referring now to FIG. 3B, illustrated is a graphical representation 318 of the scan pattern 302 based on the detector arrangement 304, in accordance with an embodiment of the present disclosure. As shown, the graphical representation 318, includes higher number of samples (data collected by detector arrangement 304) for a middle portion compared to sides. Also, the middle portion of the graphical representation 318 is wider. This enables in generation of an image (corresponding to the data of the middle portion) having uniform quality (i.e. uniform for both middle and sides of the image). Further, rotation of image (particularly, data corresponding to the image) during processing level may not influence a quality of the image.

Figure 4:
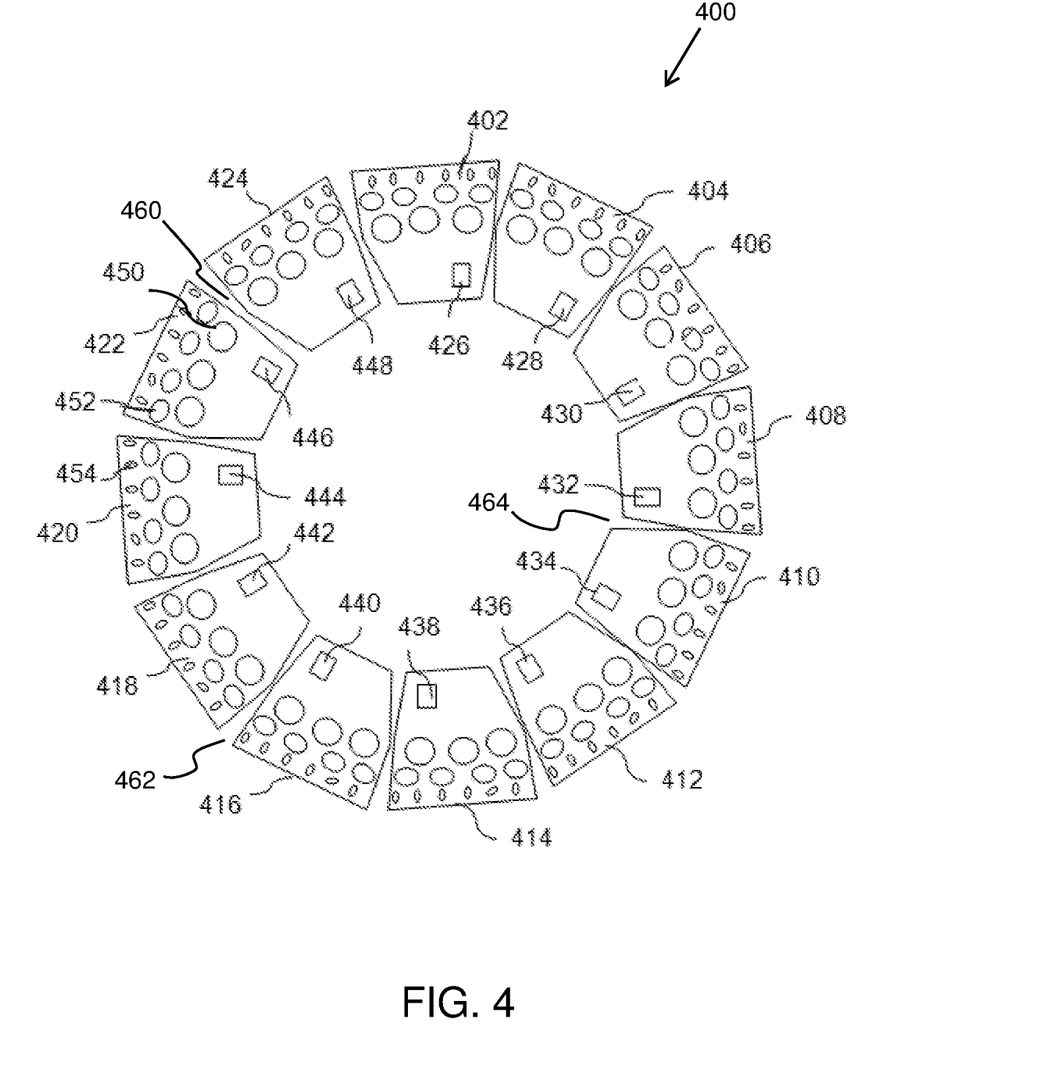
FIG. 4 is a schematic illustration of a detector arrangement for an imaging apparatus, in accordance with an embodiment of the present disclosure.

FIG. 4 is a schematic illustration of a detector arrangement 400 of an imaging apparatus (such as the imaging apparatus 200 of FIG. 2), in accordance with an embodiment of the present disclosure. As shown, the detector arrangement 400 comprises a plurality of sets of detector (or detector elements), such as detector elements 402-424 arranged in a circular manner. Further, each of the detector elements 402-424 comprises a connector, such as connectors 426-448, respectively, for electrically coupling the detector elements 402-424 to the processing unit 222 (shown in FIG. 2).

Further, each of the detector elements 402-424 comprises a plurality of detectors of multiple types. For example, as shown, each of the detector elements 402-424 comprises a first type of detectors 450, a second type of detectors 452 and a third type of detectors 454. The first type of detectors 450, the second type of detectors 452 and the third type of detectors 454 are arranged within a region 460 defined by an outer periphery 462 and an inner periphery 464 of the detector arrangement 400. Moreover, the outer and inner peripheries 462, 464 are circular in shape. Alternatively, the outer and inner peripheries 462, 464 may be substantially circular in shape, such as elliptical or oval.

As shown, the first type of detectors 450 are larger in size as compared to the second type of detectors 452, which are in turn larger in size as compared to the third type of detectors 454. The size of the first type of detectors 450, the second type of detectors 452 and the third type of detectors 454 corresponds to wavelengths of electromagnetic radiations (such as electromagnetic radiations 220, shown in FIG. 2) to be detected therewith. Further, the first type of detectors 450 are arranged towards the inner periphery 464 of the region 460 and the third type of detectors 454 are arranged towards the outer periphery 462 of the region 460, and the second type of detectors 452 are arranged therebetween. Also, as shown, the number of the first type of detectors 450 (bigger in size) is less compared to the number of the second type of detectors 452, which is in turn less in number as compared to the third type of detectors 454.

Figure 5:
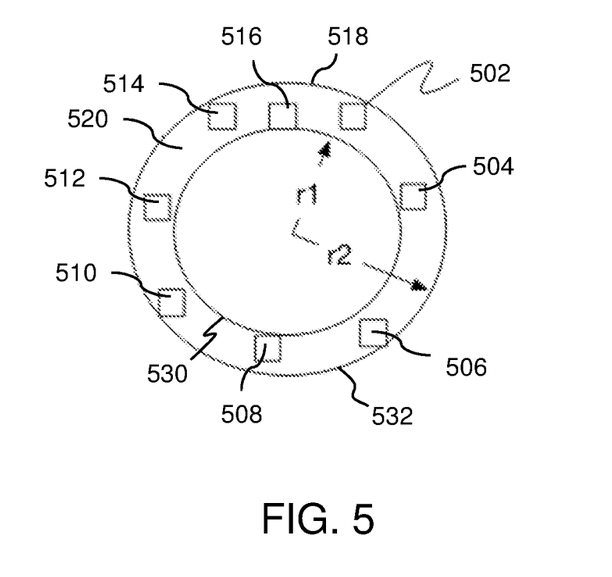
FIG. 5 is a schematic illustration of a plurality of detectors arranged in a circular form, in accordance with an embodiment of the present disclosure.

Referring now to FIG. 5, illustrated is a schematic illustration of a plurality of detectors, such as detectors 502-516, arranged in a circular form 518, in accordance with an embodiment of the present disclosure. As shown, the detectors 502-516 are arranged within a region 520 defining the circular form 518. The circular form 518 includes a radius r1 of an inner periphery 530 and a radius r2 of an outer periphery 532. Further, a ratio of the radius r2 of the outer periphery 532 to the radius r1 of the inner periphery 530 lies in a range between 1.5 and 2.

Figure 6:
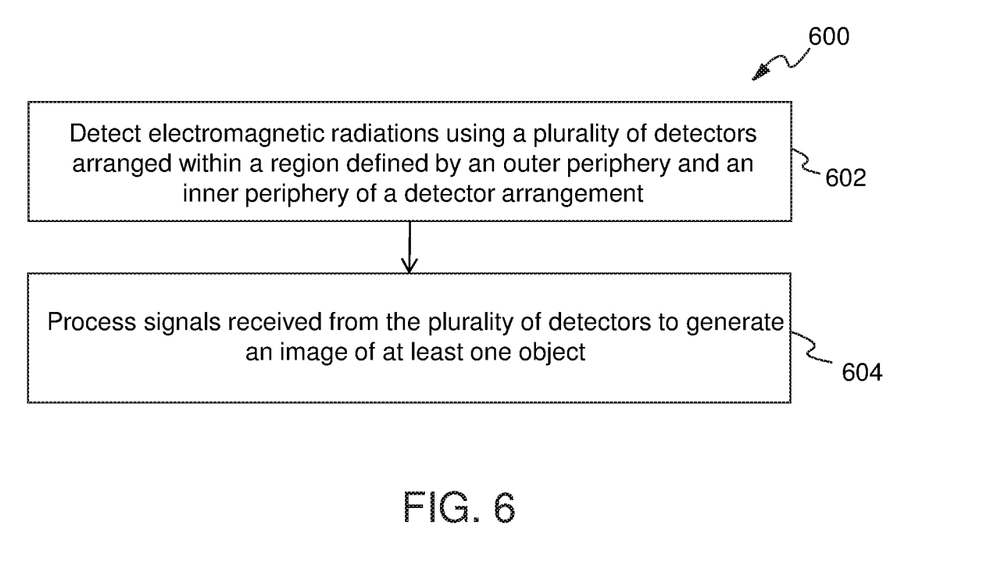
FIG. 6 is an illustration of steps of a method for monitoring objects via an imaging apparatus, in accordance with an embodiment of the present disclosure.

FIG. 6 is an illustration of steps of a method 600 for monitoring objects via an imaging apparatus, in accordance with an embodiment of the present disclosure. Specifically, the method 600 is associated with the imaging apparatus 200 (explained in conjunction with FIGS. 2-5) for monitoring the objects.

At step 602, electromagnetic radiation is detected using a plurality of detectors arranged within a region defined by an outer periphery and an inner periphery of a detector arrangement. The outer and inner peripheries are substantially circular in shape.

At step 604, signals received from the plurality of detectors are processed to generate an image of at least one object being monitored by the imaging apparatus.

Further, the steps 602 and 604 are only illustrative and other alternatives can also be provided where one or more steps are added, one or more steps are removed, or one or more steps are provided in a different sequence without departing from the scope of the claims herein. For example, in the method 600, the plurality of detectors includes at least a first type of detectors and a second type of detectors. Further, the first type of detectors is larger in size than the second type of detectors. Moreover, the size of a given detector corresponds to a wavelength of electromagnetic radiation detected by the given detector.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An imaging apparatus for scanning an object, comprising:
    a scanning mirror configured to direct electromagnetic radiation emitted from the object being scanned;
    optics; and
    a detector arrangement comprising a plurality of at least five detectors, wherein
        the plurality of at least five detectors are capable for detecting submillimeter-/millimeter-range electromagnetic radiation; and
        the plurality of at least five detectors are arranged symmetrically in a continuous circular loop in a circular shaped region about an optical axis of the optics within a region defined by an outer periphery and an inner periphery of the detector arrangement, the outer periphery and the inner periphery being arranged symmetrically about the optical axis and being circular in shape; and wherein the plurality of at least five detector are arranged within the region between the outer periphery and the inner periphery to form a circular detector arrangement arranged symmetrically about the optical axis of the optics that passes through a center of the detector arrangement.

2. An imaging apparatus according to claim 1, wherein the plurality of detectors are arranged symmetrically about an optical axis of the optics.

3. An imaging apparatus according to claim 1, wherein the plurality of detectors include at least a first type of detectors and a second type of detectors, wherein the first type of detectors are larger in size than the second type of detectors, wherein the size of a given detector corresponds to a wavelength of electromagnetic radiation detected by the given detector.

4. An imaging apparatus according to claim 3, wherein the first type of detectors are arranged towards the inner periphery of the region, and the second type of detectors are arranged towards the outer periphery of the region.

5. The imaging apparatus according to claim 4, wherein the first type of detectors are arranged in the circular shape towards the inner periphery of the region and the second type of detectors are arranged in the circular shape towards the outer periphery of the region.

6. The imaging apparatus according to claim 5, further comprising a third type of detectors arranged in the circular shape between the first type of detectors and the second type of detectors.

7. An imaging apparatus according to claim 3, wherein the number of detectors of the second type is larger than the number of detectors of the first type.

8. An imaging apparatus according to claim 1, wherein the plurality of detectors are arranged in a form of a circular loop.

9. An imaging apparatus according to claim 1, wherein a ratio of a radius of the outer periphery to a radius of the inner periphery lies in a range between 1.5 and 2.

10. An imaging apparatus according to claim 1, wherein the scanning mirror arrangement is arranged to rotate in a manner that the detector arrangement does not move when the scanning mirror arrangement rotates.

11. An imaging apparatus according to claim 1, wherein the imaging apparatus further comprises a processing unit coupled to the plurality of detectors, wherein the processing unit is configured to process signals received from the plurality of detectors to generate an image of at least one object being monitored by the imaging apparatus.

12. An imaging apparatus according to claim 1, wherein the imaging apparatus further comprises a processing unit coupled to the detector arrangement.

13. An imaging apparatus according to claim 1, wherein the scanning mirror arrangement comprises a scanning mirror and an actuator for moving the scanning mirror to direct electromagnetic radiation emitted from the object towards the optics and the plurality of detectors.

14. The imaging apparatus according to claim 13, wherein the actuator for moving the scanning mirror is configured to move the scanning mirror only when the plurality of detectors are in a fixed position.

15. The imaging apparatus according to claim 1, wherein the imaging apparatus is configured to detect other objects concealed on the object being scanned.

16. A method for monitoring objects, via an imaging apparatus comprising a detector arrangement having a plurality of at least five detectors configured to detect submillimetre/millimetre range electromagnetic radiation, the method comprising:
    directing electromagnetic radiation emitting from the object to be monitored using a scanning mirror arrangement;
    detecting the electromagnetic radiation using the plurality of at least five detectors by arranging the plurality of at least five detectors symmetrically about an optical axis of the optics within a region defined by an outer periphery and an inner periphery of the detector arrangement, the outer periphery and the inner periphery being arranged symmetrically about the optical axis and being substantially circular in shape, wherein the plurality of at least five detector are arranged within the region between the outer periphery and the inner periphery to form a circular detector arrangement arranged symmetrically about the optical axis of the optics that passes through a center of the detector arrangement; and wherein the method further comprises:

processing signals received from the plurality of at least five detectors to generate an image of at least one object being monitored by the imaging apparatus.

17. A method according to claim 16, wherein the plurality of detectors include at least a first type of detectors and a second type of detectors, wherein the first type of detectors are larger in size than the second type of detectors, wherein the size of a given detector corresponds to a wavelength of electromagnetic radiation detected by the given detector.

18. The method according to claim 17, further comprising arranging the first type of detectors in the circular shape towards the inner periphery and arranging the second type of detectors in the circular shape towards the outer periphery.

19. The method according to claim 18, further comprising arranging a third type of detector in the circular shape between the first type of detectors and the third type of detectors.

\* \* \* \* \*